US008167907B2

(12) United States Patent
Pruett et al.

(10) Patent No.: US 8,167,907 B2
(45) Date of Patent: May 1, 2012

(54) CHIROPRACTIC TABLE WITH CONTINUOUS PASSIVE MOTION

(75) Inventors: Blake Pruett, Chattanooga, TN (US); Charles Brophy, Soddy Daisy, TN (US); Durrell Martin, Lookout Mountain, GA (US)

(73) Assignee: Encore Medical Asset Corporation, Henderson, NV (US)

( * ) Notice: Subject to any disclaimer, the term of this patent is extended or adjusted under 35 U.S.C. 154(b) by 819 days.

(21) Appl. No.: 11/212,079

(22) Filed: Aug. 25, 2005

(65) Prior Publication Data

US 2006/0047237 A1 Mar. 2, 2006

Related U.S. Application Data

(60) Provisional application No. 60/604,356, filed on Aug. 25, 2004.

(51) Int. Cl.

| | |
|---|---|
| ***A61F 5/00*** | (2006.01) |
| ***A61H 1/00*** | (2006.01) |
| ***A61H 1/02*** | (2006.01) |
| ***A61H 5/00*** | (2006.01) |

(52) U.S. Cl. .......................................... 606/243; 601/26

(58) Field of Classification Search .................. 128/845; 601/23–26; 606/240–245; 602/32, 33, 36; 5/600, 607, 610–614, 617, 619, 632, 650, 5/652, 657, 658

See application file for complete search history.

(56) References Cited

U.S. PATENT DOCUMENTS

| | | | | |
|---|---|---|---|---|
| 4,523,581 | A | 6/1985 | Ekholm | |
| 4,649,905 | A * | 3/1987 | Barnes | 606/245 |
| 4,732,141 | A * | 3/1988 | Steffensmeier | 606/245 |
| 4,834,072 | A | 5/1989 | Goodman | |
| 5,123,916 | A * | 6/1992 | Riddle et al. | 606/243 |
| 5,192,306 | A | 3/1993 | Scott et al. | |
| 5,320,640 | A | 6/1994 | Riddle et al. | |
| 5,320,641 | A * | 6/1994 | Riddle et al. | 606/243 |
| 5,423,861 | A * | 6/1995 | Kelley | 606/241 |
| 5,682,327 | A * | 10/1997 | Telepko | 601/34 |
| 5,794,286 | A * | 8/1998 | Scott et al. | 5/611 |
| 5,954,750 | A | 9/1999 | Steffensmeier | |
| 6,267,735 | B1 | 7/2001 | Blanchard et al. | |
| 6,436,126 | B1 | 8/2002 | McAfee | |
| 6,547,809 | B1 | 4/2003 | Cuccia | |
| 6,638,299 | B2 | 10/2003 | Cox | |
| 6,679,905 | B2 | 1/2004 | Peetros et al. | |
| 6,821,288 | B2 * | 11/2004 | Schaeffer | 606/240 |
| 7,112,215 | B2 * | 9/2006 | Xiao et al. | 606/242 |

* cited by examiner

*Primary Examiner* — Kristen Matter

(74) *Attorney, Agent, or Firm* — Ropes & Gray LLP

(57) ABSTRACT

A therapeutic treatment table includes a plurality of table sections for supporting the body of a patient, one of which sections is a drop section. The table includes an extension/flexion section which includes a frame having a pivot axis and a terminal end, and a rotary actuator that is adapted to repeatedly pivot the frame of the extension/flexion section about the pivot axis so as to raise the terminal end of the frame during an extension phase and to lower the terminal end of the frame during a flexion phase. A mechanism is provided for setting an operational range of motion for the extension/flexion section including an operational extension limit and an operational flexion limit, so that the rotary actuator will pivot the frame of the extension/flexion section between the operational extension limit and the operational flexion limit. In a preferred embodiment of the invention, a mechanism is provided for setting a comfort zone range of motion within the operational range of motion which includes comfort zone extension limit and a comfort zone flexion limit. A comfort zone actuation switch is also provided in the preferred embodiment for switching the operation of the rotary actuator from the operational range of motion to the comfort zone range of motion, so that the rotary actuator will pivot the frame of the extension/flexion section between the comfort zone extension limit and the comfort zone flexion limit.

25 Claims, 4 Drawing Sheets

CHIROPRACTIC TABLE WITH CONTINUOUS PASSIVE MOTION

CROSS REFERENCE TO RELATED APPLICATION

This application claims the benefit of U.S. Provisional Application No. 60/604,356, which was filed on Aug. 25, 2004.

FIELD OF THE INVENTION

The present invention relates generally to medical rehabilitation devices, and more particularly to a chiropractic table that includes a section that may be repeatedly raised for extension and lowered for flexion to provide therapeutic continuous passive motion to a patient's spine.

BACKGROUND OF THE INVENTION

Chiropractic tables are known for use in treating patients suffering from a variety of orthopedic and neuropathic maladies. Such treatments include placing the patient's spine in vertical flexion (head to chest motion), extension (head to back motion), lateral flexion (left and right motion) and rotation (turning motion), as well as coupling vertical and lateral flexion to produce circumduction. Chiropractic tables are described in U.S. Pat. No. 4,523,581 of Ekholm, U.S. Pat. No. 4,649,905 of Barnes, U.S. Pat. No. 5,794,286 of Scott et al., U.S. Pat. No. 5,954,750 of Steffensmeier and U.S. Pat. No. 6,679,905 of Peetros, et al. Chiropractic tables commonly include one or more sections, some or all of which may include a drop mechanism for use in treating a particular portion of the patient's body. Generally, these drop mechanisms include an actuating mechanism that allows the table section to move abruptly and rapidly through a controlled distance when a force or pressure is applied to a body part that is supported on the table section by a chiropractor or other therapist. It is also known for a chiropractic table to include an automatic mechanism that performs cyclical flexion of the patient's spine within predetermined parameters, and such a device is described in U.S. Pat. No. 5,423,861 of Kelley.

Other treatment mechanisms of various types are known for providing therapeutic or rehabilitative manipulation of a body part. Thus, for example, U.S. Pat. No. 5,320,640 of Riddle et al. describes a device for providing continuous passive motion to the cervical spine for therapeutic or rehabilitative purposes. The Riddle device includes a stationary body support for supporting at least a portion of the patient's back, and a pivoting head support for supporting the patient's head. The head support is adapted to pivot upwardly and downwardly with respect to the stationary support to passively exercise the muscle groups surrounding the cervical spine. The Riddle device also includes a patient control device by which a patient may control the speed of pivotal movement of the head support with respect to the stationary support. However, during the operation of the Riddle device to provide continuous passive motion to the cervical spine, a patient may experience pain or sensitivity if his spine is being extended or flexed beyond an angle which is comfortable. The Riddle device does include a remote on/off switch by which the patient may stop the operation of the device, but it provides no other means or mechanism for eliminating a patient's discomfort, and no means or mechanism for eliminating a patient's discomfort while continuing to provide a therapeutic benefit.

It would be desirable, therefore, if a therapeutic device could be developed for providing continuous passive motion to a patient's spine. It would also be desirable if such a device could be provided in the form of a chiropractic or therapeutic treatment table which includes one or more drop mechanisms. It would also be desirable if such a device could be provided with means for controlling the extension and flexion of the portion of the table which moves to provide continuous passive motion to reduce such motion while still providing a therapeutic benefit.

ADVANTAGES OF THE INVENTION

Among the advantages of the invention is that it provides a therapeutic device in the form of a chiropractic table having a drop mechanism and an extension/flexion section that is capable of extending to an extension limit and flexing to a flexion limit in order to provide continuous passive motion. Another advantage of a preferred embodiment of the invention is that the range of motion of the extension/flexion section of the table may be changed from an operational range of motion to a comfort zone range of motion that imparts less extension and/or flexion than the operational range of motion. Still another advantage of a preferred embodiment of the invention is that it may automatically establish operating parameters including a comfort zone extension limit and/or a comfort zone flexion limit, as well as one or more intermediate extension limits and/or intermediate flexion limits to the range of motion, whereupon the extension/flexion section will move through a comfort zone range of motion and then through one or more intermediate ranges of motion.

Other advantages and features of this invention will become apparent from an examination of the drawings and the ensuing description.

EXPLANATION OF TECHNICAL TERMS

As used herein, the term "drop mechanism" and similar terms refer to a system or device associated with a section of a therapeutic table which includes an actuating mechanism that allows the table section to move abruptly and rapidly through a controlled distance. Preferably, the drop mechanism is actuated when an external force is applied to the table section or to a body part that is supported on the table section.

As used herein, the term "drop section" and similar terms refer to a section of a therapeutic table that includes a drop mechanism.

As used herein, the term "extension/flexion section" refers to a section of a therapeutic table that is adapted to be moved through a range of motion.

As used herein, the term "range of motion" refers to a range of angular motion between the upper extension limit and the lower flexion limit of the invention.

As used herein, the term "extension" refers to that portion of a range of motion in which the angle of the extension/flexion section of the table is increasing (in a positive direction) as the end of the extension/flexion section is raised.

As used herein, the term "extension phase" refers to that portion or phase of the operation of the invention during which extension occurs.

As used herein, the term "extension limit" refers to a limit that may be imposed during extension on the angle of the table. The term "extension limit" also refers to the angle of the extension/flexion section of a preferred embodiment of the table to which, but not beyond which, the extension/flexion section may be raised during an extension phase.

As used herein, the term “flexion” refers to that portion of a range of motion in which the angle of the extension/flexion section of the table is increasing (in a negative direction) as the end of the extension/flexion section is lowered.

As used herein, the term “flexion phase” refers to that portion or phase of the operation of the invention during which flexion occurs.

As used herein, the term “flexion limit” refers to a limit that may be imposed during flexion on the angle of the extension/flexion section. The term “flexion limit” also refers to the angle of the extension/flexion section of a preferred embodiment of the table to which, but not beyond which, extension/flexion section may be lowered during a flexion phase.

As used herein, the term “limit” may refer to either an “extension limit” or a “flexion limit”, depending on the context.

As used herein, the term “start angle” refers to the angle of the extension/flexion section of a preferred embodiment of the table from which extension begins or from which flexion begins.

As used herein, the term “flexion angle” refers to the angle of the extension/flexion section of the table at a point during a flexion phase or at a particular flexion limit.

As used herein, the term “extension angle” refers to the angle of the extension/flexion section of the table at a point during an extension phase or at a particular extension limit.

As used herein, the terms “cycle” and “operating cycle” refer to a continuous operation of the invention either from a flexion limit to an extension limit, or from an extension limit to a flexion limit.

As used herein, the term “operational extension limit” refers to an extension limit that is established for a selected range of motion.

As used herein, the term “operational flexion limit” refers to a flexion limit that is established for a selected range of motion.

As used herein, the term “rotary actuator” and similar terms refers to an electrical, hydraulic, electro-hydraulic or pneumatic device that generates a rotary force or a force that is directed along an arc.

SUMMARY OF THE INVENTION

The invention comprises a therapeutic treatment table which includes a plurality of table sections for supporting the body of a patient. At least one of these sections comprises a drop section, and at least one section comprises an extension/flexion section which includes a frame having a pivot axis and a terminal end. A rotary actuator is provided to repeatedly pivot the frame of the extension/flexion section about the pivot axis so as to raise the terminal end of the frame during an extension phase and to lower the terminal end of the frame during a flexion phase. The invention also includes means for setting a desired range of motion for the extension/flexion section including an operational extension limit and an operational flexion limit, so that the rotary actuator will pivot the frame of the extension/flexion section between the operational extension limit and the operational flexion limit. A preferred embodiment of the invention includes means for setting a start angle within the operational range of motion, and a comfort zone feature which allows a patient or therapist to set the device to decrease the angle of extension and/or flexion as the device passes through a portion of the operational range of motion. This preferred comfort zone feature includes means for setting a comfort zone range of motion comprising a comfort zone extension limit which is between the start angle and the operational extension limit and a comfort zone flexion limit which is between the start angle and the operational flexion limit, so that the rotary actuator will pivot the frame of the extension/flexion section between the comfort zone extension limit and the comfort zone flexion limit. In this embodiment, a comfort zone actuation switch is also provided for switching the operation of the rotary actuator from the operational range of motion to the comfort zone range of motion.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which.

DESCRIPTION OF THE PREFERRED EMBODIMENTS OF THE INVENTION

Figure 1:
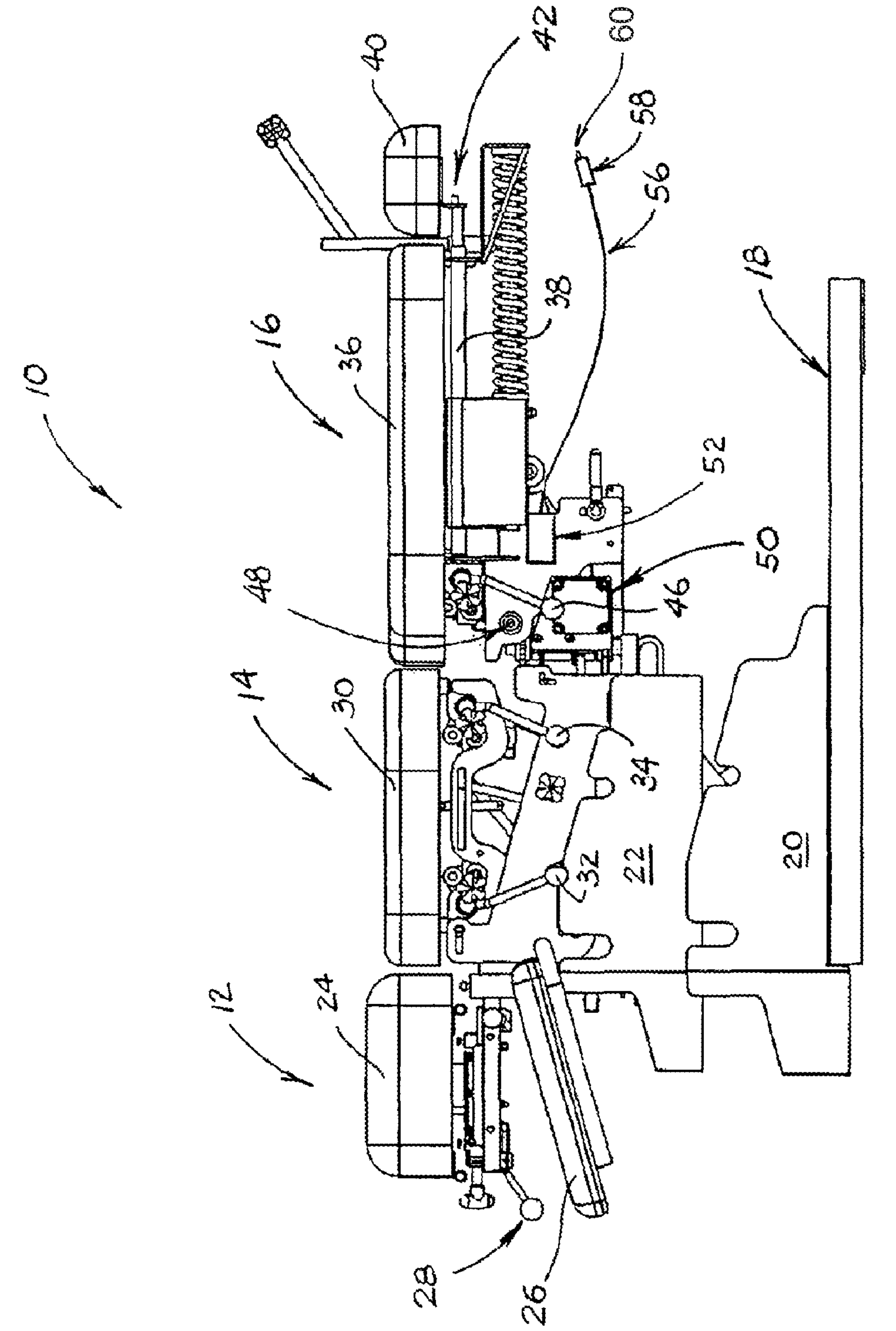
FIG. 1 is a side view of a preferred embodiment of the invention, showing the extension/flexion section in a neutral (horizontal) attitude.
Figure 2:
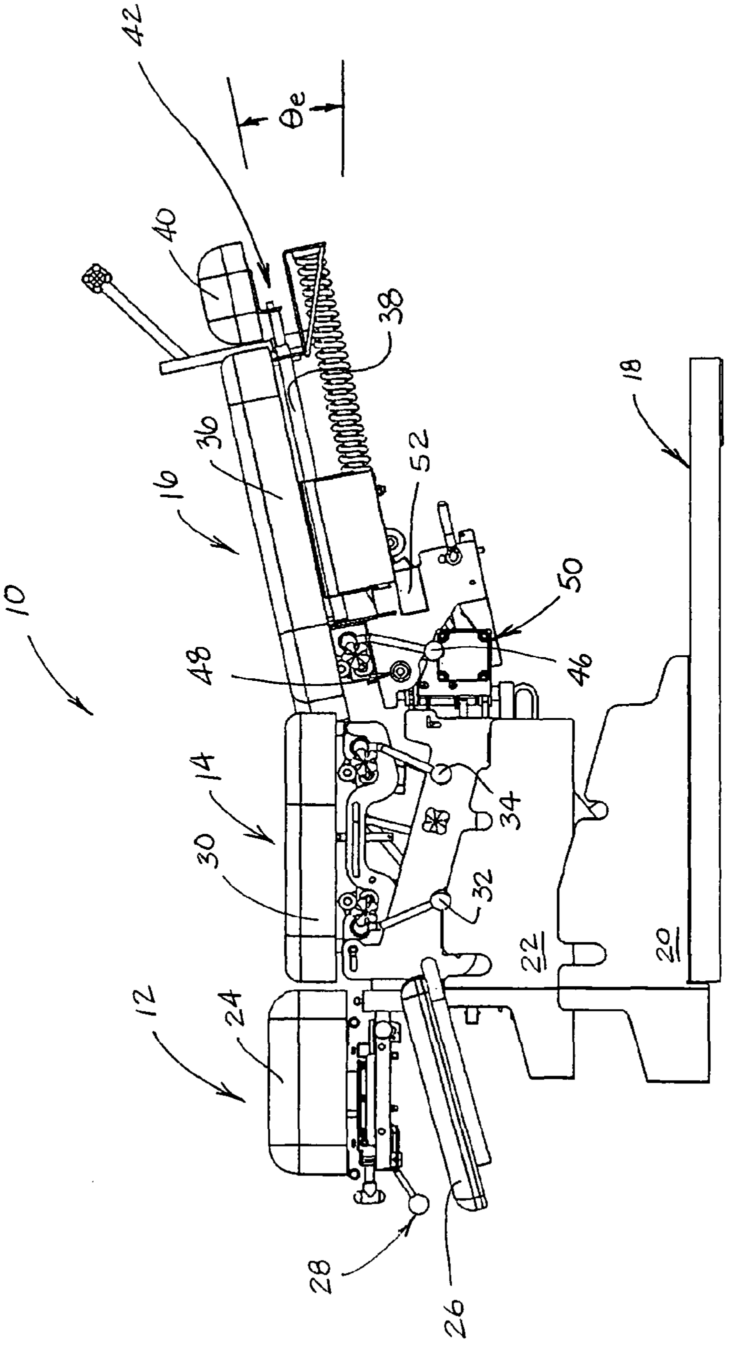
FIG. 2 is a side view of the chiropractic table of FIG. 1 showing the extension/flexion section at an extension limit.
Figure 3:
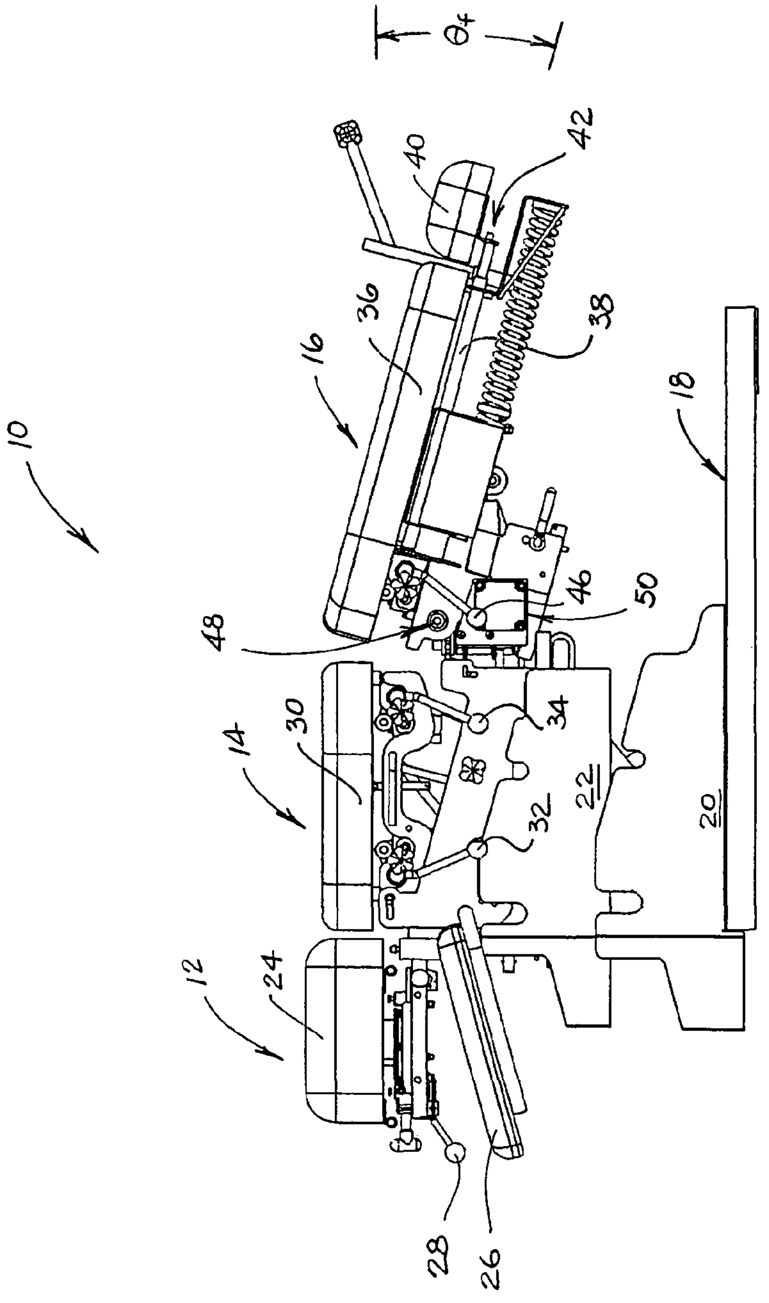
FIG. 3 is a side view of the chiropractic table of FIGS. 1 and 2 showing the extension/flexion section at a flexion limit.

Referring now to the drawings, FIGS. 1-3 illustrate a preferred embodiment of a chiropractic table or therapeutic treatment table 10 having head section 12, midsection 14 and rear section 16. In this embodiment of the invention, head section 12 is adapted to support the head and cervical spine of a patient, and sections 14 and 16 are adapted to support the remaining portions of the body including the portions below the cervical spine. All three sections 12, 14 and 16 of this embodiment are elevated above table base 18. Preferably, the elevation of the table sections is adjustable in a manner known to those having ordinary skill in the art to which the invention relates. Table 10 also includes lower base cover 20 and upper base cover 22. The upper base cover slides within the lower base cover when the table is lowered to its base elevation (not shown).

Head section 12 includes face cushion 24 and a pair of arm cushions, only one of which, cushion 26, is shown in the drawings. Head section 12 also includes a conventional cervical drop mechanism including forward drop actuation knob 28. Midsection 14 includes chest/lumbar cushion 30 and a pair of conventional drop mechanisms including thoracic drop actuation knob 32 and lumbar drop actuation knob 34. Rear section 16 includes pelvic cushion 36 which is mounted on a frame, a portion 38 of which is illustrated in the drawings. Rear section 16 also includes foot cushion 40 which is mounted on the frame at its terminal end 42. Preferred rear section 16 also includes a conventional pelvic drop mechanism including pelvic drop actuation knob 46. Although the preferred embodiment of the invention includes a head section with a single drop mechanism, a midsection with a pair of drop mechanisms and a rear section with a single drop mechanism, any of the three table sections may include one or more drop mechanisms, as is known to those having ordinary skill in the art to which the invention relates.

Preferred rear section 16 also comprises an extension/flexion section which includes pivot axis 48 and rotary actuator 50 which may be operated to repeatedly pivot the frame of section 16 about the pivot axis so as to raise the terminal end of the frame during an extension phase (illustrated in FIG. 2) and to lower the terminal end of the frame during a flexion phase (illustrated in FIG. 3). Rotary actuator 50 may comprise a reciprocating drive assembly including a motor, a transmission (or gearbox) and a push rod such as is illustrated in U.S. Pat. No. 5,423,861 of Kelley or other rotary drive mechanism as is known to those having ordinary skill in the art to which the invention relates.

The preferred embodiment of the invention includes a microprocessor or computer controller 52 such as is known generally to those having ordinary skill in the art to which the invention relates. Controller 52 is mounted to the frame of the rear section (as shown) or is connected by suitable wiring to a separate control pedestal (not shown) and preferably includes control panel 54 (shown in FIGS. 4 and 5), which is described in more detail hereinafter. In the alternative, controller 52 may be mounted to the frame of the table and connected by wiring or by wireless means to control panel 54. In the preferred embodiment of the invention that is illustrated in the drawings, control cord 56 is provided to connect the controller to control pendant 58 (not shown in FIGS. 2 and 3) which allows the patient to access the controller in order to initiate the preferred comfort zone feature of the invention. It is also contemplated that the control panel may provide a setting that allows the controller to be accessed by foot pedals mounted on the base of the table (not shown). Various combinations of controller 52 with control panel 54, control pendant 58 and the aforementioned foot pedals provide means for setting the various operating parameters and for controlling the various functions of the preferred embodiment of the invention, as will be described in more detail hereinafter.

The invention thus includes means for setting an operational range of motion for the extension/flexion section including an operational extension limit and an operational flexion limit, so that the rotary actuator will pivot the frame of the extension/flexion section between the operational extension limit and the operational flexion limit. Preferably, the invention also includes means for setting a start angle, the angle from which extension and/or flexion begins, within the operational range of motion. Preferably, the start angle is set at 0° (the neutral or horizontal attitude or position). FIG. 1 shows extension/flexion section 16 in a neutral or horizontal attitude in which frame portion 38 is generally horizontal and parallel to table base 18. FIG. 2 shows extension/flexion section 16 in a condition of extension and FIG. 3 shows section 16 in a condition of flexion.

The operational extension limit corresponds to an operational extension angle $\theta_e$ (see FIG. 2) which is described by the angle of the extension/flexion section, as measured from the start angle (preferably 0°, as shown in FIG. 2), as its terminal end is raised to the end of an extension phase. The operational flexion limit corresponds to an operational flexion angle $\theta_f$ (see FIG. 3) which is described by the angle of the extension/flexion section, as measured from the start angle (preferably 0°, as shown in FIG. 3), as its terminal end is lowered to the end of a flexion phase. The preferred control means for setting a desired range of motion in the illustrated embodiment includes limit switches (not shown) or other means to insure that when the rotary actuator moves the extension/flexion section to an extension limit, it will reverse direction and move towards the flexion limit. Similarly, when the extension/flexion section is moved to a flexion limit, the rotary actuator will reverse direction and move towards an extension limit.

In a preferred embodiment of the invention, rear section 16 can be raised (in the extension phase) to an operational extension limit corresponding to an angle of +14° or less (relative to the neutral or horizontal of FIG. 1) in the manual mode (when treatment to provide continuous passive motion to the spine is supervised by a health care professional) or to an operational extension limit corresponding to an angle of +12° or less in the automatic mode (when treatment to provide continuous passive motion to the spine is unsupervised). Similarly, the rear section can be lowered (in the flexion phase) to an operational flexion limit corresponding to an angle of −17° or less (relative to the neutral or horizontal of FIG. 1) in the manual mode or to an operational flexion limit corresponding to an angle of −15° or less in the automatic mode. In this preferred embodiment of the invention, therefore, depending on the patient's circumstances, the operational extension limit and the operational flexion limit can be set at any angle between +14° and −17° in the manual mode or at any angle between +12° and −15° in the automatic mode. Similarly, the start angle, at which flexion and/or extension are set to begin, may be set at any point within these limits.

During a treatment session, especially during an unsupervised treatment session, a patient may experience pain as his spine is extended and/or flexed. Under such circumstances, the patient may activate a comfort zone feature by pressing a switch such as switch 60 on pendant 58. In the alternative (although not shown in the drawings), a comfort zone actuation switch may be mounted on arm cushion 26. In a first embodiment of the invention, controller 52 is programmed so that pressing switch 60 once will simply stop the rear section. In a second embodiment, controller 52 is programmed so that pressing switch 60 once will cause the rear section to move to a start angle, such as the neutral or horizontal position (0°) of FIG. 1 or any other position within the operational range of motion. For example, controller 52 may be programmed so that pressing switch 60 once will cause the rear section to move to a start angle comprising the midpoint between the operational extension limit and the operational flexion limit that is currently in use. In this embodiment for example, if the operational extension limit were set at +8° and the operational flexion limit were set at −14°, the rear section would move to the midpoint between these limits, or to −3°. Regardless of which of these features were programmed into controller 52 for movement of the rear section upon pressing switch 60 once, it is contemplated that pressing switch 60 twice in succession will activate the comfort zone feature of a preferred embodiment of the invention. When the preferred comfort zone feature is activated according to the invention, the range of motion through which the extension/flexion section moves is temporarily reduced.

Consequently, the preferred embodiment of the invention includes means (comprising various combinations of controller 52 with control panel 54, control pendant 58 and the foot pedals) for setting a comfort zone range of motion within the operational range of motion. This comfort zone range of motion comprises a comfort zone extension limit which is equal to or less than (i.e. nearer to the start angle or the horizontal or neutral position) the operational extension limit and a comfort zone flexion limit which is equal to or less than (i.e. nearer to the start angle or the horizontal or neutral position) the operational flexion limit. If a start angle has been set, the comfort zone extension limit will be no further from the start angle than the operational extension limit and the comfort zone flexion limit will be no further from the start angle than the operational flexion limit. Obviously, one or preferably both of the comfort zone limits will be nearer to the start angle than the corresponding operational limit if the patient is to receive relief from the pain associated with operation through the entire operational range of motion.

As described above in connection with a preferred embodiment of the invention, pressing comfort zone actuation switch 60 once will stop the movement of the rear section or move it to an intermediate position (or start angle) within the operational range of motion. Pressing switch 60 twice will switch the operation of the rotary actuator from the operational range of motion to the comfort zone range of motion, so that the rotary actuator will pivot the frame of the extension/flexion section between the comfort zone extension limit and the comfort zone flexion limit. The controller can be programmed so that the extension and flexion limits are reduced from the operational limits by a percentage or by a fixed number of degrees. For example, if the operational extension limit were set at +8° and the operational flexion limit were set at −14°, the controller might be programmed to set the comfort zone limits to cycle the rear section between a comfort zone extension limit of +6° (75% of +8°) and a comfort zone flexion limit of −10.5° (75% of −14°). In another embodiment of the comfort zone feature, if the extension limit were set at +8° and the flexion limit were set at −14°, the controller might be programmed to cycle the rear section between a comfort zone extension limit of +5° (3° short of +8°) and a comfort zone flexion limit of −11° (3° short of −14°).

It is also preferred that various intermediate limits be set by the controller so that the rear section can cycle between an extension limit that increases from the comfort zone extension limit to the operational extension limit (i.e. moves closer to the operational extension limit) in a number of graduated steps and a flexion limit that increases from the comfort zone flexion limit to the operational flexion limit (i.e. moves closer to the operational flexion limit) in a number of graduated steps. For example, if the operational extension limit were set at +8° and the operational flexion limit were set at −14°, the controller might be programmed to cycle the rear section between a comfort zone extension limit of +6° (75% of +8°) and a comfort zone flexion limit of −10.5° (75% of −14°) for a predetermined period of time or a predetermined number of cycles. Thereafter, the controller could be programmed to cycle the rear section between a first intermediate extension limit of +6.5° and a first intermediate flexion limit of −11.375° in a first step (for one or more cycles), between a second intermediate extension limit of +7.0° and a second intermediate flexion limit of −12.25° in a second step (for one or more cycles), between a third intermediate extension limit of +7.5° and a third intermediate flexion limit of −13.125° in a third step (for one or more cycles), and between the operational extension limit of +8.0° and the operational flexion limit of −14° in a fourth step.

In an alternative embodiment of the comfort zone feature, the controller might be programmed to cycle the rear section between a comfort zone extension limit of +6° (75% of +8°) and a comfort zone flexion limit of −10.5° (75% of −14°) for a predetermined period of time or a predetermined number of cycles. Thereafter, the controller could be programmed to cycle the rear section between a first intermediate extension limit of +7.0° and a first intermediate flexion limit of −11.0° in a first step (for one or more cycles), between a second intermediate extension limit of +7.5° and a second intermediate flexion limit of −11.5° in a second step (for one or more cycles), between the operational extension limit of +8.0° and a third intermediate flexion limit of −12.0° in a third step (for one or more cycles), between the operational extension limit of +8.0° and a fourth intermediate flexion limit from of −12.5° in a fourth step (for one or more cycles), between the operational extension limit of +8.0° and a fifth intermediate flexion limit of −13.0° in a fifth step (for one or more cycles), between the operational extension limit of +8.0° and a sixth intermediate flexion limit of −13.5° in a sixth step (for one or more cycles), and between the operational extension limit of +8.0° and the operational flexion limit of −14.0° in a seventh step.

In another embodiment of the comfort zone feature, if the operational extension limit were set at +8° and the operational flexion limit were set at −14°, the controller might be programmed to cycle the rear section between a comfort zone extension limit of +5° (3° short of +8°) and a comfort zone flexion limit of −11° (3° short of −14°) for one or more cycles. Thereafter, the controller could be programmed to cycle the rear section between a first intermediate extension limit of +6° and a first intermediate flexion limit of −12° in a first step (for one or more cycles), between a second intermediate extension limit of +7° and a second intermediate flexion limit of −13° in a second step (for one or more cycles), and between the operational extension limit of +8° and the operational flexion limit of −14° in a third step.

In a preferred embodiment of the invention, means are provided for setting the operating parameters for various operating cycles, including an operational range of motion, a comfort zone range of motion, an intermediate range of motion, an operational cycle speed (i.e. the speed at which the rear section cycles through the operational range of motion just prior to actuation of the comfort zone feature), a comfort zone cycle speed (i.e. the speed at which the rear section cycles through the comfort zone range of motion) that is below the operational cycle speed, and an intermediate cycle speed (i.e. the speed at which the rear section cycles through the intermediate range of motion) that is no lower than the comfort zone cycle speed and below the operational cycle speed. In this embodiment of the invention, activating the comfort zone feature will cause the rear section to cycle through the comfort zone range of motion at the comfort zone cycle speed, which, for example, may be programmed to be 50% of the operational cycle speed.

In one version of this embodiment of the invention, the speed at which the rear section cycles through the comfort zone range of motion and any intermediate ranges of motion is gradually increased as the range of motion approaches the operational range of motion. Thus for example, if the operational extension limit were set at +8° and the operational flexion limit were set at −14°, the controller may be programmed to cycle the rear section between a comfort zone extension limit of +4° (50% of +8°) and a comfort zone flexion limit of −7° (50% of −14°) at a comfort zone cycle speed equal to 50% of the operational cycle speed for a predetermined period of time or a predetermined number of cycles. Thereafter, the controller could be programmed to cycle the rear section between a first intermediate extension limit of +5° and a first intermediate flexion limit of −8° at a speed of 60% of the operational cycle speed in a first step (for one or more cycles), between a second intermediate extension limit of +6° and a second intermediate flexion limit of −9° at a speed of 70% of the operational cycle speed in a second step (for one or more cycles), between a third intermediate extension limit of +7° and a third intermediate flexion limit of −10° at a speed of 80% of the operational cycle speed in a third step, and between the operational extension limit of +8° and the operational flexion limit of −11° at the operational cycle speed in a fourth step.

In another version of this embodiment of the invention, the comfort zone cycle speed may be maintained as the rear section cycles through the comfort zone range of motion and any intermediate ranges of motion until the operational range of motion is reached. Thereafter, the speed may be increased in a series of steps as the rear section continues to cycle through the operational range of motion. Thus for example, if the comfort zone cycle speed were programmed to be 50% of the operational cycle speed, the operational extension limit were set at +8° and the operational flexion limit were set at −14°, the controller may be programmed to cycle the rear section between a comfort zone extension limit of +4° (50% of +8°) and a comfort zone flexion limit of −7° (50% of −14°) at a comfort zone cycle speed equal to 50% of the operational cycle speed for a predetermined period of time or a predetermined number of cycles. Thereafter, the controller could be programmed to cycle the rear section between a first intermediate extension limit of +5° and a first intermediate flexion limit of −8° at the comfort zone cycle speed (i.e. 50% of the operational cycle speed) in a first step (for one or more cycles), between a second intermediate extension limit of +6° and a second intermediate flexion limit of −9° at the comfort zone cycle speed in a second step (for one or more cycles), between a third intermediate extension limit of +7° and a third intermediate flexion limit of −10° at the comfort zone cycle speed in a third step, and between the operational extension limit of +8° and the operational flexion limit of −11° at the comfort zone cycle speed in a fourth step (for one or more cycles). Thereafter, the controller could be programmed to cycle the rear section between the operational extension limit of +8° and the operational flexion limit of −11° at a speed of 60% of the operational cycle speed in a fifth step (for one or more cycles), between the operational extension limit of +8° and the operational flexion limit of −11° at a speed of 70% of the operational cycle speed in a sixth step (for one or more cycles), between the operational extension limit of +8° and the operational flexion limit of −11° at a speed of 80% of the operational cycle speed in a seventh step, and between the operational extension limit of +8° and the operational flexion limit of −11° at the operational cycle speed thereafter.

The comfort zone feature thus allows a patient to obtain relief from pain experienced during extension and/or flexion, while allowing him to continue with a treatment session and to progress gradually to the operational extension and flexion limits at which pain was encountered.

Figure 4:
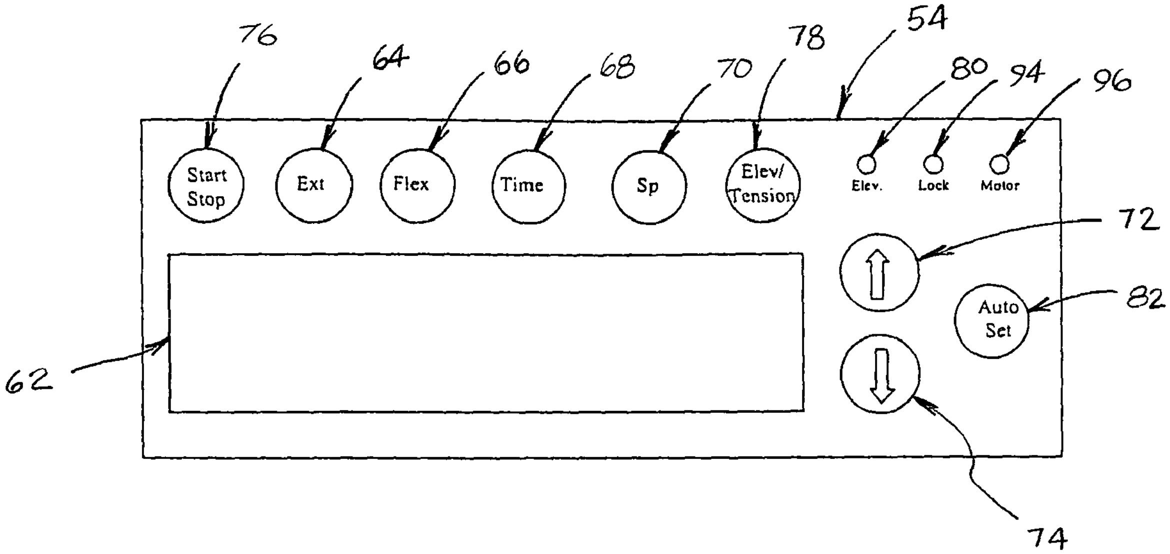
FIG. 4 is a schematic view of a control panel for a preferred embodiment of the invention.
Figure 5:
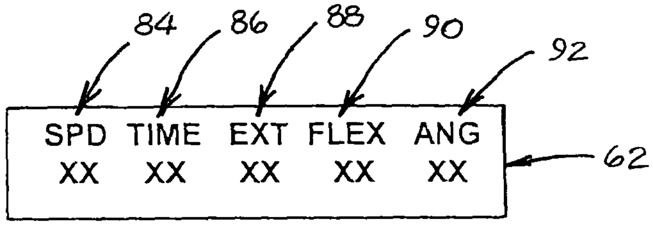
FIG. 5 is a schematic view of a display for certain of the operating parameters of a preferred embodiment of the invention.

Referring now to FIGS. 4 and 5, preferred control panel 54, which includes display screen 62, is shown. A user may enter an edit mode to set (or change from a previous or default setting) any of various functions of preferred table 10 by pressing "Ext" function button 64, "Flex" function button 66, "Time" function button 68 or "Sp" function button 70. By pressing "Ext" function button 64, the function "Set Extension Angle" will be displayed on screen 62, and the arrow up and arrow down buttons, 72 and 74 respectively, may be pressed one or more times to change the previous setting (or the programmed default setting) of the operational extension angle. Similarly, by pressing "Flex" function button 66, the function "Set Flexion Angle" will be displayed on screen 62, and the arrow up and arrow down buttons, 72 and 74 respectively, may be pressed one or more times to change the previous setting (or the programmed default setting) of the operational flexion angle. In a similar manner, pressing "Time" function button 68 will display the function "Set Time" on screen 62, and the arrow up and arrow down buttons, 72 and 74 respectively, may be pressed one or more times to change the previous setting (or the programmed default setting) of the treatment time. Similarly, by pressing "Sp" function button 70, the function "Set Speed" will be displayed on screen 62, and the arrow up and arrow down buttons, 72 and 74 respectively, may be pressed one or more times to change the previous setting (or the programmed default setting) of the speed of the movement of the rear table section through the programmed operational range of motion. When the desired setting for any of these parameters is obtained, the function button may be pressed a second time to exit from the edit or function setting mode, or the user may press another function button to set or change another functional parameter. In one embodiment of the invention, the operating parameters for the comfort zone range of motion and any intermediate ranges of motion may be set in a similar manner. In another embodiment of the invention, the operating parameters for the comfort zone range of motion and any intermediate ranges of motion may be preset within the controller.

In a preferred embodiment of the invention, if the controller is not in the edit mode, pressing up arrow button 72 will increase the speed at which the rear section of the table cycles through its range of motion. Similarly, pressing the down button 74 will reduce the operational speed. Pressing "Start/Stop" button 76 will start or stop the automatic cycling of the rear section of the table by which continuous passive motion is provided. "Elev/Tension" button 78 can be depressed to enable the "elevation" feature by which the foot pedals can be used to raise or lower the table relative to the base, or to disable such feature. When the "elevation" feature is activated, LED 80 will be illuminated, and the foot pedals on the machine can be used to change the elevation of the table. If the "elevation" feature is disabled, LED light 80 will not be illuminated, and the foot pedals can be used to begin and control extension and flexion in the manual mode. In a preferred embodiment of the invention, unless the foot pedals are used to begin extension and flexion in the manual mode within fifteen seconds after the "Elev/Tension" button is pressed, the elevation feature will automatically activate and LED 80 will be illuminated.

"Auto/Set" button 82 can be depressed to allow the user to progress through the automatic (continuous passive motion) extension/flexion menu and edit the settings for the various operating parameters. When a particular setting is selected, as displayed on screen 62 (shown in detail in FIG. 5), the display symbol for that particular setting will flash, indicating that it can be changed by pressing either "up arrow" button 72 to increase the value of the setting or "down arrow" button 74 to decrease the value of the setting. Thus, as shown in FIG. 5, "SPD" display 84 indicates the speed of operation during extension and/or flexion, and "TIME" display 86 indicates the treatment time. "EXT" display 88 indicates the operational extension limit, and "FLEX" display 90 indicates the operational flexion limit. "ANG" display 92 indicates the instantaneous angle of extension/flexion section 16 with respect to the neutral or horizontal attitude (0°) shown in FIG. 1, as measured by a potentiometer (not shown) on rear section 16, at any time during operation of the table. After all the settings for the various parameters are selected and set, pressing the "Start/Stop" button 76 activate the automatic extension/flexion operation of the machine.

Preferably, rear section 16 will include a mechanical stop at the highest extension angle of the table. A limit switch (not shown) at the location of this mechanical stop will brake the motor (also not shown) which operates rotary actuator 50 in case of a malfunction, and will hold the angular position of the rear section until the "Start/Stop" button is depressed. Similarly, rear section 16 will include a mechanical stop at the lowest available flexion angle of the table. A limit switch (not shown) at the location of this mechanical stop will brake the motor (also not shown) which operates rotary actuator 50 in case of a malfunction, and will hold the angular position of the rear section until the "Start/Stop" button is depressed. If either of these limit switches have locked the machine, LED 94 will be illuminated. It is also preferred that a switch (not shown) be located on the push rod (also not shown) of the motor (also not shown) which comprise a preferred embodiment of rotary actuator 50, which switch will sense if the motor is engaged. If so, LED 96 will be illuminated.

It is also preferred that controller 52 includes a memory unit that will retain the most recent settings of the operating parameters for the extension/flexion (continuous passive motion) feature. It is also preferred that a calibration feature be included (also not shown) so that a calibration mode can be selected to permit the operating parameters of the machine to be calibrated or to permit the machine to be serviced.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations, and the same are intended to be comprehended within the meaning and range of equivalents of the appended claims.

What is claimed is:

1. A therapeutic treatment table comprising:
- (a) a plurality of table sections for supporting the body of a patient, comprising:
  - (i) a drop section;
  - (ii) an extension/flexion section for supporting a portion of the body below the cervical spine, which section comprises a frame and a cushion, the frame having a pivot axis and a terminal end;
- (b) a rotary actuator that is adapted to repeatedly pivot the frame of the extension/flexion section about the pivot axis so as to raise the terminal end of the frame during an extension phase and to lower the terminal end of the frame during a flexion phase;
- (c) a controller operably connected to the rotary actuator and programmable to:
  - store a first set of operating parameters including an operational range of motion for the extension/flexion section, wherein the operational range of motion includes an operational extension limit and an operational flexion limit, so that the rotary actuator will pivot the frame of the extension/flexion section between the operational extension limit and the operational flexion limit, and
  - store a second set of operating parameters including a comfort zone range of motion within the operational range of motion, said comfort zone range of motion including a comfort zone extension limit and a comfort zone flexion limit; and
- (d) an actuation switch connected to the controller, wherein in response to activating the activation switch during a treatment session while the rotary actuator is operating according to the first set of operational parameters, the controller retrieves the second set of operating parameters and configures the operation of the rotary actuator according to the second set of operating parameters, and wherein the first and second set of operating parameters are stored before activating the activation switch.

2. The therapeutic treatment table of claim 1 wherein the extension/flexion section also includes a drop mechanism.

3. The therapeutic treatment table of claim 2 wherein the drop mechanism of the extension/flexion section is disposed above the pivot axis.

4. The therapeutic treatment table of claim 3 wherein the drop mechanism of the extension/flexion section is disposed below the interior end of the cushion and adjacent the pivot axis.

5. The therapeutic treatment table of claim 1 which includes:
- (a) means for setting an operational cycle speed at which the rotary actuator will pivot the frame of the extension/flexion section between the operational extension limit and the operational flexion limit;
- (b) means for setting a comfort zone cycle speed at which the rotary actuator will pivot the frame of the extension/flexion section between the comfort zone extension limit and the comfort zone flexion limit, which comfort zone cycle speed is reduced from the operational cycle speed.

6. The therapeutic treatment table of claim 1 which includes means for setting a comfort zone extension limit which is a predetermined percentage below the operational extension limit and a comfort zone flexion limit which is a predetermined percentage above the operational flexion limit.

7. The therapeutic treatment table of claim 1 which includes means for setting a comfort zone extension limit which is a predetermined number of degrees below the operational extension limit and a comfort zone flexion limit which is a predetermined number of degrees above the operational flexion limit.

8. The therapeutic treatment table of claim 1 which includes:
- (a) means for setting a start angle within the operational range of motion for the extension/flexion section;

wherein the comfort zone extension limit is no further from the start angle than the operational extension limit and the comfort zone flexion limit is no further from the start angle than the operational flexion limit;

and wherein the actuation switch:
- (i) moves the extension/flexion section to the start angle; and
- (ii) switches the operation of the rotary actuator from the operational range of motion to the comfort zone range of motion, so that the rotary actuator will pivot the frame of the extension/flexion section between the comfort zone extension limit and the comfort zone flexion limit.

9. The therapeutic treatment table of claim 8 which includes means for setting the start angle at 0°.

10. The therapeutic treatment table of claim 8 which includes means for setting the start angle at the midpoint between the operational extension limit and the operational flexion limit.

11. The therapeutic treatment table of claim 1 which includes:
- (a) means for setting a start angle within the operational range of motion for the extension/flexion section;

wherein the comfort zone extension limit is between the start angle and the operational extension limit and the comfort zone flexion limit is between the start angle and the operational flexion limit;

and wherein the actuation switch:
- (i) moves the extension/flexion section to the start angle;
- (ii) switches the operation of the rotary actuator from the operational range of motion to the comfort zone range of motion, so that the rotary actuator will pivot the frame of the extension/flexion section between the comfort zone extension limit and the comfort zone flexion limit.

12. The therapeutic treatment table of claim 11 which includes:

(a) means for setting a first intermediate range of motion, which includes a first intermediate extension limit between the comfort zone extension limit and the operational extension limit and a first intermediate flexion limit between the comfort zone flexion limit and the operational flexion limit;

(b) means for setting a second intermediate range of motion, which includes a second intermediate extension limit between the first intermediate extension limit and the operational extension limit and a second intermediate flexion limit between the first intermediate flexion limit and the operational flexion limit;

(c) means for switching the operation of the rotary actuator from the comfort zone range of motion to the first intermediate range of motion;

(d) means for switching the operation of the rotary actuator from the first intermediate range of motion to the second intermediate range of motion;

(e) means for switching the operation of the rotary actuator from the second intermediate range of motion to the operational range of motion.

13. The therapeutic treatment table of claim 11 which includes:

(a) means for setting an intermediate range of motion which includes an intermediate extension limit between the comfort zone extension limit and the operational extension limit and an intermediate flexion limit between the comfort zone flexion limit and the operational extension limit;

(b) means for switching the operation of the rotary actuator from the comfort zone range of motion to the intermediate range of motion;

(c) means for switching the operation of the rotary actuator from the intermediate range of motion to the operational range of motion.

14. The therapeutic treatment table of claim 13 which includes:

(a) means for setting an operational cycle speed at which the rotary actuator will pivot the frame of the extension/flexion section between the operational extension limit and the operational flexion limit;

(b) means for setting a comfort zone cycle speed at which the rotary actuator will pivot the frame of the extension/flexion section between the comfort zone extension limit and the comfort zone flexion limit, which comfort zone cycle speed is reduced from the operational cycle speed;

(c) means for setting an intermediate cycle speed at which the rotary actuator will pivot the frame of the extension/flexion section between the intermediate extension limit and the intermediate flexion limit, which intermediate cycle speed is reduced from the operational cycle speed.

15. The therapeutic treatment table of claim 11 which includes:

(a) means for setting a first set of operating parameters for an operating cycle, said first set of operating parameters comprising:

(i) the operational range of motion for the extension/flexion section including the operational extension limit and the operational flexion limit;

(ii) a first operational cycle speed at which the rotary actuator will pivot the frame of the extension/flexion section between the operational extension limit and the operational flexion limit;

(b) means for setting a second set of operating parameters for an operating cycle, said second set of operating parameters comprising:

(i) the comfort zone range of motion comprising the comfort zone extension limit and the comfort zone flexion limit;

(ii) a comfort zone cycle speed at which the rotary actuator will pivot the frame of the extension/flexion section between the comfort zone extension limit and the comfort zone flexion limit, which comfort zone cycle speed is reduced from the operational cycle speed;

(c) means for setting a third set of operating parameters for an operating cycle, said third set of operating parameters comprising:

(i) an intermediate range of motion which includes an intermediate extension limit between the comfort zone extension limit and the operational extension limit and an intermediate flexion limit between the comfort zone flexion limit and the operational extension limit;

(ii) a first intermediate cycle speed at which the rotary actuator will pivot the frame of the extension/flexion section between the intermediate extension limit and the intermediate flexion limit, which first intermediate cycle speed is reduced from the operational cycle speed;

(d) means for operating the rotary actuator according to the first set of operating parameters;

(e) means for operating the rotary actuator according to the second set of operating parameters;

(f) means for operating the rotary actuator according to the third set of operating parameters.

16. The therapeutic treatment table of claim 11 which includes:

(a) means for setting a first set of operating parameters for an operating cycle, said first set of operating parameters comprising:

(i) the operational range of motion for the extension/flexion section including the operational extension limit and the operational flexion limit;

(ii) a first operational cycle speed at which the rotary actuator will pivot the frame of the extension/flexion section between the operational extension limit and the operational flexion limit;

(b) means for setting a second set of operating parameters for an operating cycle, said second set of operating parameters comprising:

(i) the comfort zone range of motion comprising the comfort zone extension limit and the comfort zone flexion limit;

(ii) a comfort zone cycle speed at which the rotary actuator will pivot the frame of the extension/flexion section between the comfort zone extension limit and the comfort zone flexion limit, which comfort zone cycle speed is reduced from the first operational cycle speed;

(c) means for setting a third set of operating parameters for an operating cycle, said third set of operating parameters comprising:

(i) an intermediate range of motion which includes an intermediate extension limit between the comfort zone extension limit and the operational extension limit and an intermediate flexion limit between the comfort zone flexion limit and the operational extension limit;

(ii) a first intermediate cycle speed at which the rotary actuator will pivot the frame of the extension/flexion section between the intermediate extension limit and the intermediate flexion limit, which first intermediate cycle speed is reduced from the first operational cycle speed;

(d) means for setting a fourth set of operating parameters for an operating cycle, said fourth set of operating parameters comprising:

(i) the operational range of motion which includes the operational extension limit and the operational flexion limit;

(ii) a second intermediate cycle speed at which the rotary actuator will pivot the frame of the extension/flexion section between the operational extension limit and the operational flexion limit, which second intermediate cycle speed is greater than the comfort zone cycle speed and less than the first operational cycle speed;

(e) means for operating the rotary actuator according to the first set of operating parameters;

(f) means for operating the rotary actuator according to the second set of operating parameters;

(g) means for operating the rotary actuator according to the third set of operating parameters;

(h) means for operating the rotary actuator according to the fourth set of operating parameters.

17. The therapeutic treatment table of claim 1, wherein the controller includes controls configured to switch the operation of the rotary actuator from the operational range of motion to the comfort zone range of motion during a treatment session.

18. The therapeutic treatment table of claim 1, wherein the actuation switch is housed by a hand-held control pendant.

19. A therapeutic treatment table comprising:

(a) a plurality of table sections for supporting the body of a patient, comprising:

(i) a drop section;

(ii) an extension/flexion section comprising a frame and a cushion, the frame having a pivot axis and a terminal end;

(b) a rotary actuator that is adapted to repeatedly pivot the frame of the extension/flexion section about the pivot axis so as to raise the terminal end of the frame during an extension phase and to lower the terminal end of the frame during a flexion phase;

(c) a controller operably connected to the rotary actuator and programmable to:

store a first set of operating parameters for an operating cycle, said first set of operating parameters comprising:

(i) an operational range of motion for the extension/flexion section including an operational extension limit and an operational flexion limit;

(ii) an operational cycle speed at which the rotary actuator will pivot the frame of the extension/flexion section between the operational extension limit and the operational flexion limit; and store a second set of operating parameters for an operating cycle, said second set of operating parameters comprising:

(i) a comfort zone range of motion within the operational range of motion, said comfort zone range of motion comprising a comfort zone extension limit and a comfort zone flexion limit;

(ii) a comfort zone cycle speed at which the rotary actuator will pivot the frame of the extension/flexion section between the comfort zone extension limit and the comfort zone flexion limit, which comfort zone cycle speed is reduced from the operational cycle speed;

(d) an actuation switch connected to the controller, wherein in response to activating the activation switch during a treatment session while the rotary actuator is operating according to the first set of operational parameters, the controller retrieves the second set of operating parameters and configures the operation of the rotary actuator according to the second set of operating parameters, and wherein the first and second set of operating parameters are stored before activating the activation switch.

20. The therapeutic treatment table of claim 19 wherein the extension/flexion section also includes a drop mechanism.

21. The therapeutic treatment table of claim 19 wherein the controller operates to set the comfort zone cycle speed at 50% of the operational cycle speed.

22. The therapeutic treatment table of claim 19 wherein the controller is programmable to:

set a third set of operating parameters for an operating cycle, said third set of operating parameters comprising:

(i) a first intermediate range of motion, which includes a first intermediate extension limit between the comfort zone extension limit and the operational extension limit and a first intermediate flexion limit between the comfort zone flexion limit and the operational flexion limit;

(ii) a first intermediate cycle speed at which the rotary actuator will pivot the frame of the extension/flexion section between the first intermediate extension limit and the first intermediate flexion limit, which first intermediate cycle speed is reduced from the operational cycle speed;

set a fourth set of operating parameters for an operating cycle, said fourth set of operating parameters comprising:

(i) a second intermediate range of motion, which includes a second intermediate extension limit between the first intermediate extension limit and the operational extension limit and a second intermediate flexion limit between the first intermediate flexion limit and the operational flexion limit;

(ii) a second intermediate cycle speed at which the rotary actuator will pivot the frame of the extension/flexion section between the second intermediate extension limit and the second intermediate flexion limit, which second intermediate cycle speed is reduced from the operational cycle speed;

(c) means for switching the operation of the rotary actuator from the second set of operational parameters to the third set of operational parameters;

(d) means for switching the operation of the rotary actuator from the third set of operational parameters to the fourth set of operational parameters;

(e) means for switching the operation of the rotary actuator from the fourth set of operational parameters to the first set of operational parameters.

23. The therapeutic treatment table of claim 22:

(a) wherein the controller operates to set the comfort zone cycle speed at 50% of the operational cycle speed;

(b) wherein the controller operates to set the first intermediate cycle speed at a level no lower than the comfort zone cycle speed and below the operational cycle speed;

(c) wherein the controller operates to set the second intermediate cycle speed at a level no lower than the comfort zone cycle speed and below the operational cycle speed.

24. The therapeutic treatment table of claim 19, wherein the controller includes controls configured to switch the operation of the rotary actuator from the operational range of motion to the comfort zone range of motion during a treatment session.

25. The therapeutic treatment table of claim 19, wherein the actuation switch is housed by a hand-held control pendant.

* * * * *